United States Patent [19]
Markoll

[11] Patent Number: 6,119,631
[45] Date of Patent: Sep. 19, 2000

[54] COIL CABINET FOR TREATING ANIMALS WITH MAGNETIC FIELD THERAPY

[76] Inventor: Richard Markoll, 17791 Saxony Ct., Boca Raton, Fla. 33496

[21] Appl. No.: 09/283,854

[22] Filed: Apr. 1, 1999

[51] Int. Cl.[7] ............................. A01K 1/03; A61N 1/00
[52] U.S. Cl. .............................. 119/417; 600/13
[58] Field of Search ..................... 119/417, 673, 119/452, 678; 312/236, 108, 109; 128/845; 600/9, 13

[56] References Cited

U.S. PATENT DOCUMENTS

| | | | |
|---|---|---|---|
| 1,714,635 | 5/1929 | Schafer | 119/678 |
| 3,861,179 | 1/1975 | Orchard | 68/6 |
| 3,872,342 | 3/1975 | Dankert | 312/290 |
| 3,915,151 | 10/1975 | Kraus | 600/13 |
| 3,941,092 | 3/1976 | Winters | 119/673 |
| 4,665,898 | 5/1987 | Costa et al. | 600/14 |
| 5,131,904 | 7/1992 | Markoll | 600/14 |
| 5,453,073 | 9/1995 | Markoll | 600/14 |
| 5,605,344 | 2/1997 | Insalaco et al. | 280/47.34 |
| 5,693,004 | 12/1997 | Carlson et al. | 601/23 |

*Primary Examiner*—Peter M. Poon
*Assistant Examiner*—Yvonne R. Abbott
*Attorney, Agent, or Firm*—Dallett Hoopes

[57] ABSTRACT

Cabinet has wheeled base with hinged outward wing panels at the same level as the lower end of a coil into which an animal may be placed for treatment with a pulsed magnetic field. Leg units hingedly support the distal ends of the wing panels.

5 Claims, 4 Drawing Sheets

COIL CABINET FOR TREATING ANIMALS WITH MAGNETIC FIELD THERAPY

FIELD OF THE INVENTION

This invention relates to a cabinet for treating animals with magnetic field therapy. The cabinet is at once a protective and concealing device for the treatment coil and control yet offers, when in use position, support for the affected animal being treated.

BACKGROUND OF THE INVENTION

In U.S. Pat. No. 5,131,904 to Richard Markoll is disclosed an apparatus and treatment for diseased organs with magnetic field therapy. The diseases referred to in the Markoll patent and related patents are arthritis and sports-type injuries, although the prospect of such treatment and apparatus suggest other possibilities.

While most early work with the Markoll apparatus and process was with humans, the diseased organs of animals have also been the subject of treatment and, there is, a need for an apparatus to facilitate such treatment on animals.

SUMMARY OF THE INVENTION

The present invention fits this need. The invention is a coil cabinet for treating animals with magnetic field therapy and comprises a rectangular wheeled base. The base supports an annular coil. Outward wing panels are hingedly secured to opposite sides of the base, the wing panels having upward fences at opposite ends thereof. Downward leg units are hingedly secured along the distal ends of the respective wing panels, the leg units each comprising a bearing panel hinged back against the underside of the associated wing panel, a perpendicular downward support panel and end panels, each secured to the respective adjacent ends of the bearing panel and support panels.

In use, the wing panels form a planar horizontal animal supporting platform intercepted by the coil. In storage, the wing panels can be hinged up and the leg units folded up and over to form a closed rectangular solid.

BRIEF DESCRIPTION OF THE DRAWINGS

Further objects and features of the invention will be clear to those skilled in the art from a review of the following specification and drawings, all of which present a non-limiting form of the invention. In the drawings.

DESCRIPTION OF THE PREFERRED EMBODIMENT

Figure 1:
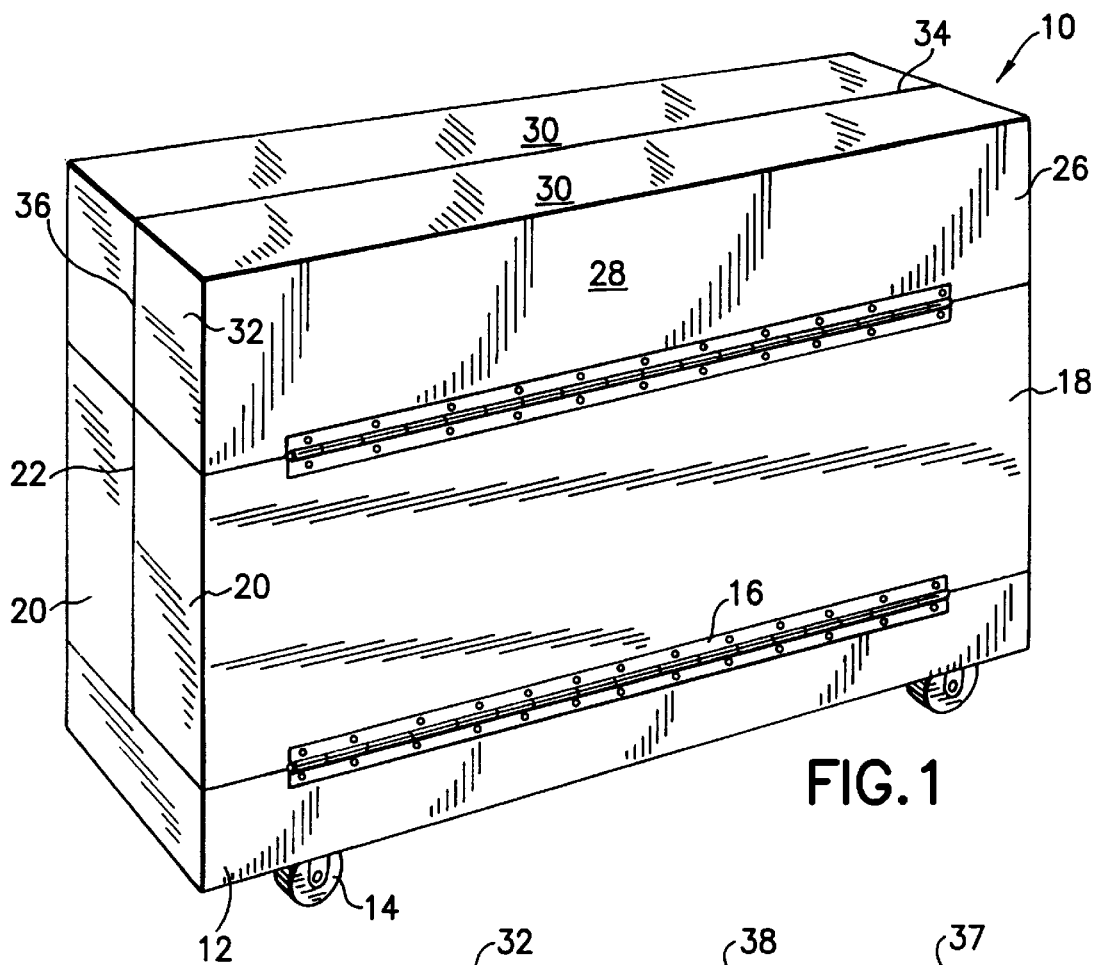
FIG. 1 is a perspective view of a coil cabinet for treating animals with magnetic field therapy embodying the invention.
Figure 2:
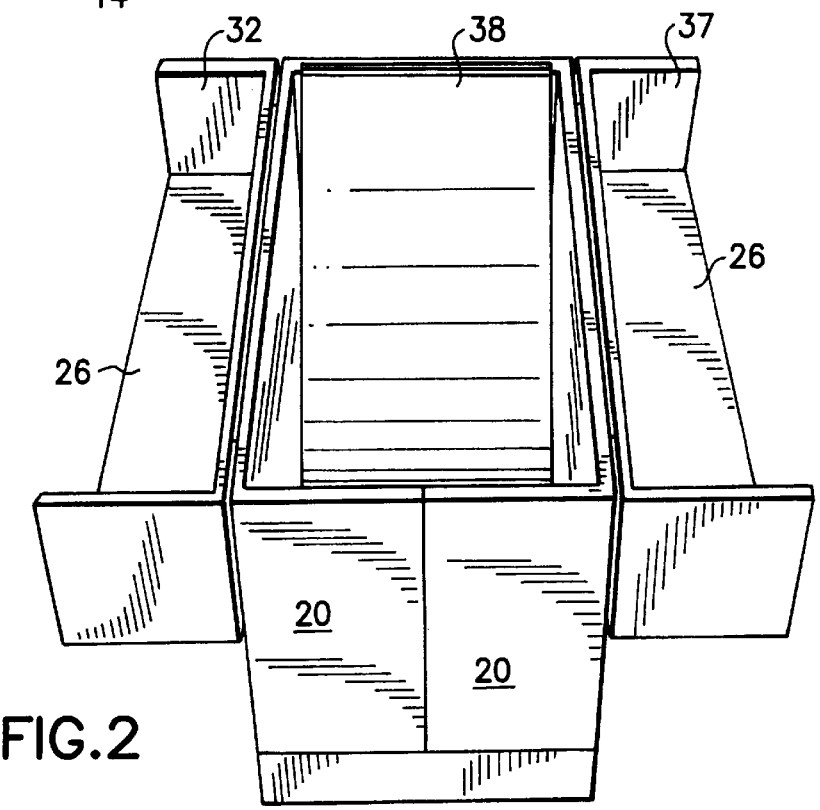
FIG. 2 is a perspective view showing the cabinet with the leg units hinged open.

A coil cabinet embodying the invention is shown in FIG. 1 and generally designated 10. It comprises a base 12 having wheels 14, some or all of which may be swingably mounted on the bottom of the base. Hingedly supported on opposite sides of the base 12 by piano-type hinges 16 are the wing panels 18. Each wing panel is formed with perpendicular fences 20 on the respective opposite sides. In the condition shown in FIG. 1, the ends of the fences 20 on the wing panels 18 are contiguous along a contact line 22.

Hingedly secured to the distal ends of the respective wing panels 18, again by piano-type hinges 24, are leg units 26. Each leg unit comprises a bearing panel 28, a support panel 30 and opposite end panels 32. With the cabinet in the condition shown in FIG. 1, the support panels have edges that are contiguous along a contact line 34 and, similarly, the end panels 32 are contiguous along the contact line 36.

As shown in FIG. 1, the cabinet is thus a wheeled rectangular solid in which the hinged parts are fully extended and corresponding parts on opposite sides of the cabinet are contiguous along contact lines. A latch, if desired or necessary, may be connected to the opposite support panels 30 to hold them in the closed condition shown in FIG. 1.

Figure 3:
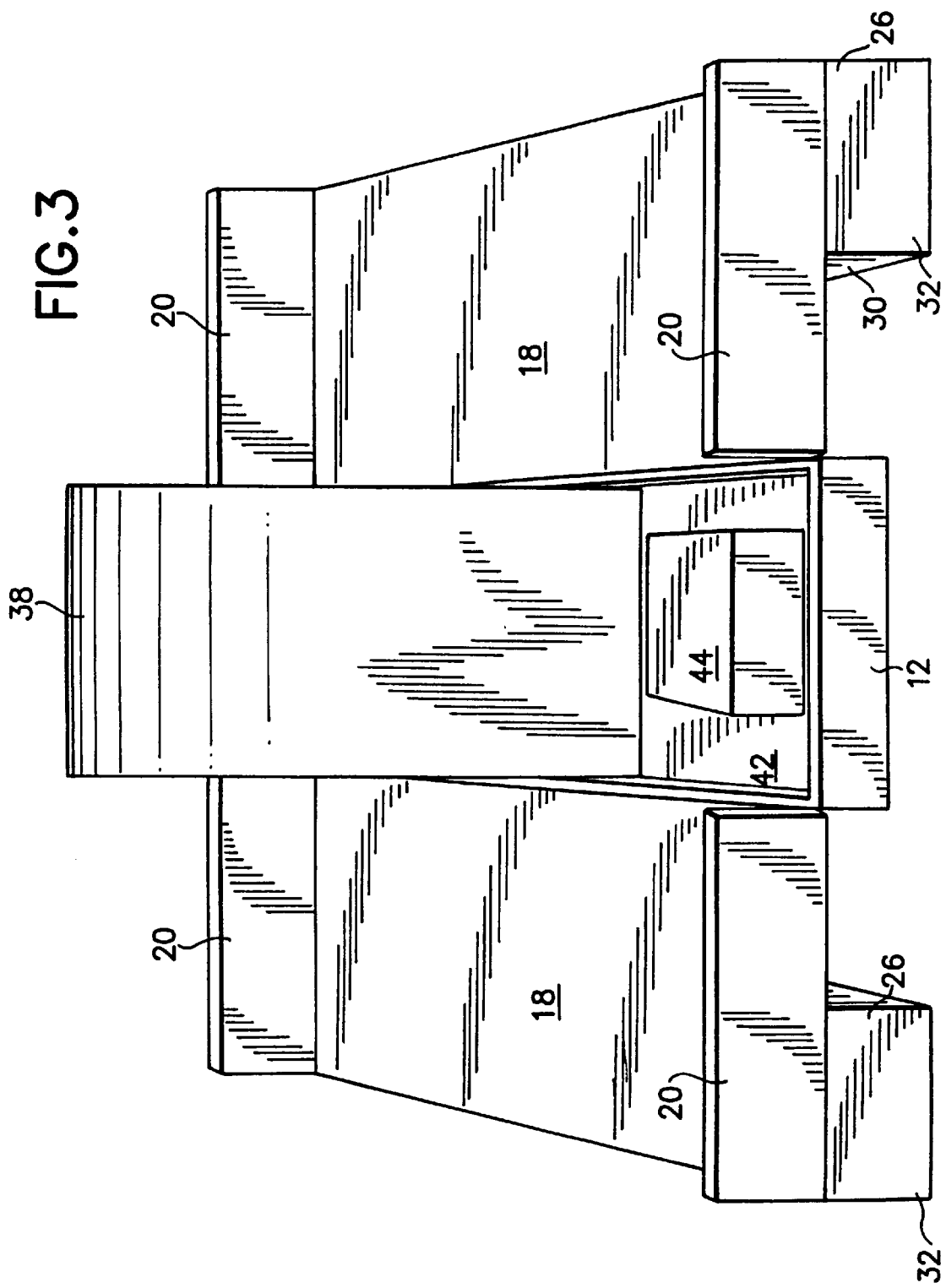
FIG. 3 is a perspective view of the cabinet showing the wing panels pivoted open and the leg units thereunder.
Figure 4:
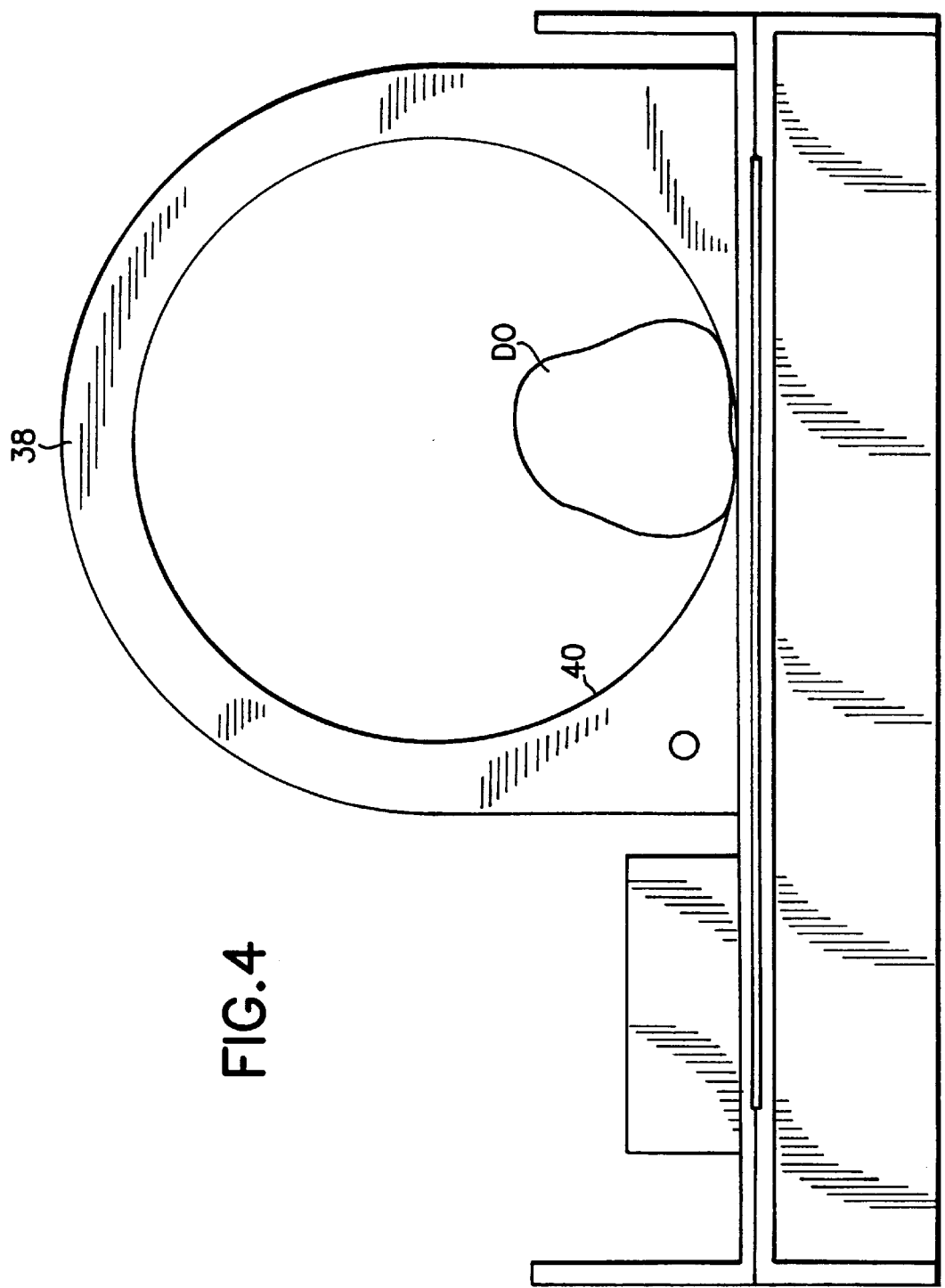
FIG. 4 is a side elevational view.
Figure 5:
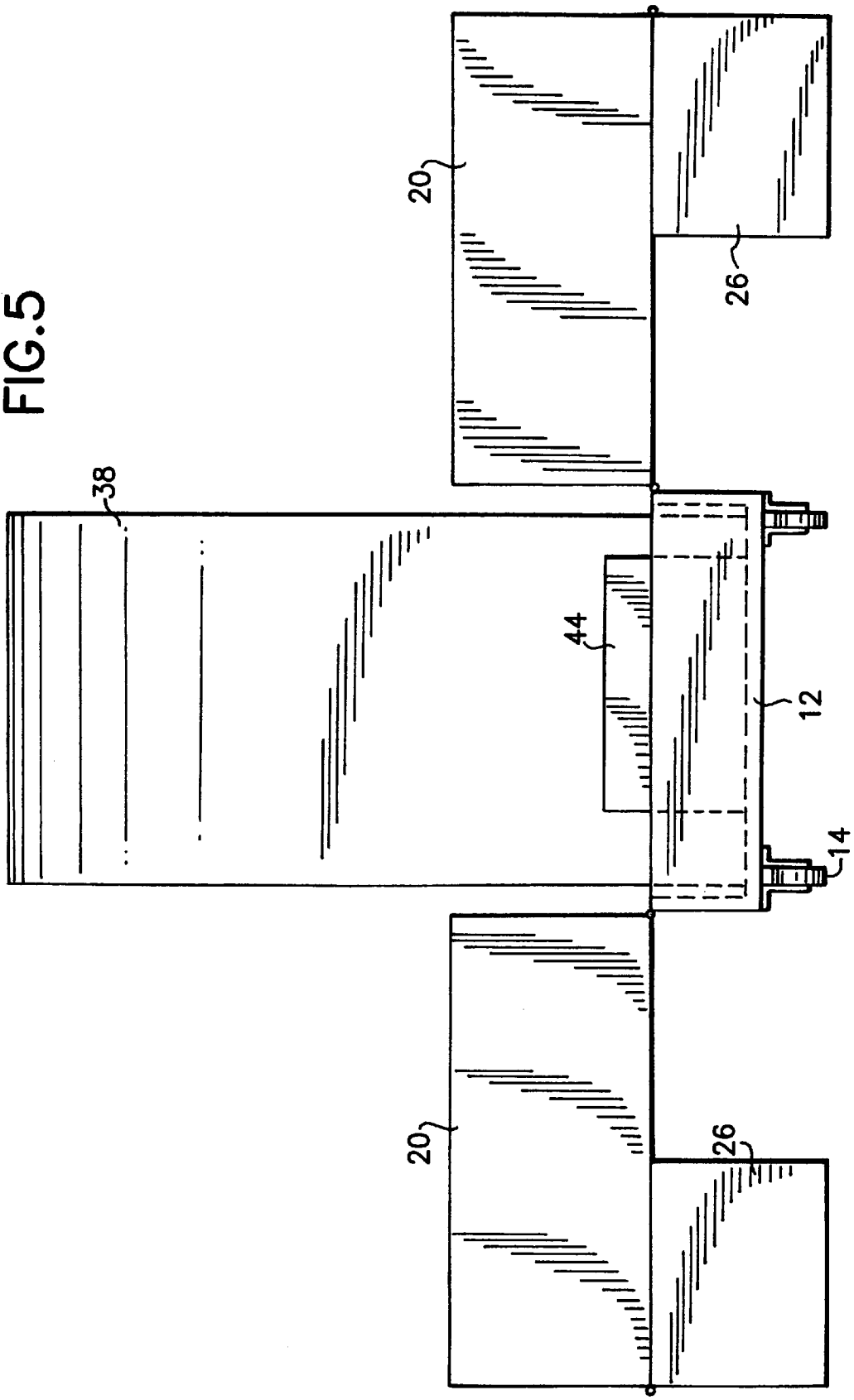
FIG. 5 is a front elevational view of the cabinet in fully open position.

The first step in preparing the cabinet for use is to unlatch the latch (not shown) holding the support panels 30 together. The leg units are pivoted about the hinges 24 so that the bearing panels 28 engage against the outward face of the wing panels 18 (FIG. 3). This reveals the top of the coil 38.

The next step in preparing the cabinet for use is to pivot the wing panels 18 about the hinges 16. This leaves the cabinet in the condition shown in FIG. 3 wherein the wing panels 18 constitute a planar platform, the top surface of which is at the level of the bottom of the opening 40 in the coil 38. This leaves the fences 20 extending upward to form a kind of curb in the opposite ends of the wing panels 18. The leg units 26 are now disposed under the distal ends of the wing panels 18, and the support panels 30 and the end panels 32 serve to support the wing panels 18. As shown, the base 12 may include a bottom wall 42 so that the sides of the base form a margin therearound. As shown, the base supports the coil 38 and the control box 44 for the coil including a power supply as described in the above-mentioned Markoll patent.

In use, with the cabinet in the condition shown in FIG. 3, the animal is placed on one of the wing panels 18 and slid so that the part of the animal with the diseased organ to be treated is disposed within the opening 40 of the coil 38. Illustratively, this is presented in outline schematic form designated DO.

It should be clear that the cabinet thus presented offers a neat mobile package combining a protective and aesthetic enclosure for the coil 38 when in storage condition and, at the same time, when in use condition, provides a substantial support for the animal during the treatment.

Variations in the invention are possible. Thus, while the invention has been shown in only one embodiment, it is not so limited but is of a scope defined by the following claim language which may be broadened by an extension of the right to exclude others from making, using or selling the invention as is appropriate under the doctrine of equivalents.

What is claimed is:

1. A coil cabinet for treating animals with magnetic field therapy comprising:
   a. a rectangular wheeled base;
   b. an annular coil supported on the base;
   c. outward wing panels hingedly secured to the base at opposite sides of the coil respectively, the wing panels having upward fences at opposite ends thereof respectively; and
   d. downward leg units hingedly secured along the distal ends of the respective wing panels, the leg units each comprising a bearing panel hinged back against the underside of the adjacent wing panel, a perpendicular downward support panel and opposite end panels each secured to the respective adjacent ends of the bearing panels and support panels;
wherein in use, the wing panels form a planar horizontal animal-supporting platform intercepted by the coil, and, in storage, the wing panels can be hinged up and the leg units folded up and over so that the fences of the respective wing panels and the end panels and leg panels of the respective leg units are contiguous to form a closed wheeled rectangular case.

2. A coil cabinet as claimed in claim 1 wherein the hinged securements are piano-type hinges.

3. A coil cabinet as claimed in claim 1 wherein the wheels are at the corners of the base.

4. A coil cabinet as claimed in claim 1 wherein the coil has an opening and the bottom of the opening is on a level with the platform.

5. A coil cabinet as claimed in claim 1 wherein a power supply is supported on the base adjacent the coil.

* * * * *